(12) United States Patent
Lee et al.

(10) Patent No.: US 8,596,149 B2
(45) Date of Patent: Dec. 3, 2013

(54) SEQUENTIAL SAMPLER FOR RUNOFF WATER

(75) Inventors: Bong Joo Lee, Daejeon (KR); Yong Je Kim, Daejeon (KR)

(73) Assignee: Korea Institute of Geoscience and Mineral Resources, Daejeon-Si (KR)

( * ) Notice: Subject to any disclaimer, the term of this patent is extended or adjusted under 35 U.S.C. 154(b) by 410 days.

(21) Appl. No.: 13/161,665

(22) Filed: Jun. 16, 2011

(65) Prior Publication Data

US 2012/0144936 A1   Jun. 14, 2012

(30) Foreign Application Priority Data

Sep. 17, 2010   (KR) .................. 10-2010-0091873

(51) Int. Cl.
*G01N 1/00*   (2006.01)

(52) U.S. Cl.
USPC ........................................... 73/864.31

(58) Field of Classification Search
USPC ............... 73/864.31, 864.63, 864.65, 864.66
See application file for complete search history.

(56) References Cited

U.S. PATENT DOCUMENTS

| | | | |
|---|---|---|---|
| 4,958,528 A | 9/1990 | Garrison | |
| 5,347,877 A | 9/1994 | Gadbois | |
| 5,463,909 A | 11/1995 | Eldridge | |
| 7,066,021 B1 | 6/2006 | Noe | |
| 8,429,986 B2 * | 4/2013 | Lee et al. | 73/864 |
| 2006/0082262 A1 * | 4/2006 | DeMarco et al. | 312/199 |
| 2013/0214469 A1 * | 8/2013 | Terzini | 269/287 |

* cited by examiner

*Primary Examiner* — Hezron E Williams
*Assistant Examiner* — Mark A Shabman
(74) *Attorney, Agent, or Firm* — Hershkovitz & Associates, PLLC; Abraham Hershkovitz

(57) ABSTRACT

A sequential sampler for runoff water. The sampler includes a rail member installed to be sloped downward in one direction; a plurality of storage members that move to a downward direction of the rail member; a stopper installed at a middle portion of the rail member that intermits a movement of the storage members; a device of supplying runoff water and inducing drop of storage cylinder that drops runoff water inside of the storage member stood by at a front portion of the stopper and drops the storage cylinder of the storage member stored with the runoff water after elapsing a predetermined time; and an intake pump of runoff water.

5 Claims, 5 Drawing Sheets

SEQUENTIAL SAMPLER FOR RUNOFF WATER

CROSS-REFERENCE TO RELATED PATENT APPLICATION

This application claims the benefit under 35 U.S.C. §119 to Korean Patent Application No. 10-2010-0091873, filed on Sep. 17, 2010, in the Korean Intellectual Property Office, the disclosure of which is incorporated herein in its entirety by reference.

BACKGROUND OF THE INVENTION

1. Field of the Invention

The present invention relates to a sampler, capable of sampling runoff water sequentially according to a predetermined time interval.

2. Description of the Related Art

To recycle rain water as alternate water resources and to reduce inflowing of nonpoint pollution to rivers or underground by surface runoff, runoff water quality must be managed and maintained to be above a certain level. For this, research on the first flush phenomenon is necessary. The first flush is a phenomenon that is associated with the occurrence that the first portion of stormwater runoff is the most contaminated. Therefore, research of water-treatment or separating and excluding initial stage runoff is actively conducted.

To accurately analyze variations of rainwater qualities with time, it needs to sample rainwater, at regular intervals, from the point of time when rainfall starts to the point of time when rainfall stops, and a sealing of sample bottle to prevent evaporation of collected runoff water sample and loss of volatile organic compounds.

SUMMARY OF THE INVENTION

To solve the above problems, it is therefore an object of the present invention to provide a sequential sampler for runoff water, capable of automatically sensing rain outflow from ground surface and sampling the runoff water sequentially according to a predetermined time. When it rains, a plurality of storage members are allowed to move downward along a downward-sloped rail member. A stopper is installed at a middle portion of the rail member. An electric actuator separates a storage cylinder apart from the storage member so that only the storage member separated with the storage cylinder passes the stopper. That is, the object of the present invention is to provide a sequential sampler for runoff water that performs a continuous process of sampling runoff water according to a users predetermined time by performing a process of passing the storage member separated with the storage cylinder through the stopper. The storage cylinder and the storage member are connected by hydraulic coupler. Therefore, the separation of storage cylinder from the storage member means a separation of a socket and a plug of the hydraulic coupler, which acts as a means to seal the storage cylinder.

The objects and advantages of the present invention will be described below and will be known by embodiments of the present invention. The objects and advantages of the present invention will be embodied by the means and its combinations represented in the claims.

The present invention, a sequential sampler for runoff water as means to solve above problems includes: a rail member (10) installed to be sloped downward toward one direction; a storage member (20) mounted to the rail member (10) that moves in downward direction and is configured of a storage cylinder (21) formed with a coupler unit (25) at an upper end portion of the storage member (20); a stopper (30) installed at a middle portion of the rail member (10) to intermit a transfer of the storage member (20); a device of supplying runoff water and inducing drop of storage cylinder (40) disposed at a front portion of the stopper (30) to inflow runoff water to the storage member (20) and to separate the storage cylinder (21) of the storage member (20) completed with runoff water inflow; and an intake pump (50) to supply and provide runoff water for the device of supplying runoff water and inducing drop of storage cylinder (40).

Further, the storage member (20) includes; the storage cylinder (21) provided with a shutter (22) at a lower end portion of the storage member (20); the coupler unit (25) including a plug (23) coupled integrally at an upper end portion of the storage cylinder (21) and a socket (24) correspondingly and detachably coupled with the plug (23); a driver (28) formed rotatable and extended to both sides of the socket (24) to correspond with the rail member (10); and a wire (29) connecting the socket (24) and the storage cylinder (21).

Further, the device of supplying runoff water and inducing drop of storage cylinder (40) includes; an electric actuator unit (41) that moves up and down; and, an inlet (43) that operates up and down movement together with the electric actuator unit (41) at a lower end portion of the electric actuator unit (41) and moves down to press and separate the socket (24) of the connecting member from the plug (23).

Further, the stopper (30) includes a path way (31) open in vertical direction at a middle portion, the path way (31) has a width (W) smaller than a diameter (D) of the storage cylinder (21) so that the storage member (20) passes only when the storage cylinder (21) is separated and dangled at the socket (24) of the coupler unit (25) by the wire (29).

Further, the device of supplying runoff water and inducing drop of storage cylinder (40) includes; a controller (60) that sequentially samples and collects runoff water in the plurality of storage members (20) at a predetermined time interval set by a user through controlling moving up and down operation of the electric actuator unit (41), according to whether there is rainfall or not.

BRIEF DESCRIPTION OF THE DRAWINGS

The above and other features and advantages of the present invention will become more apparent by describing in detail exemplary embodiments thereof with reference to the attached drawings in which.

BRIEF DESCRIPTION OF REFERENCE NUMBERS OF MAJOR ELEMENTS

Figure 1:
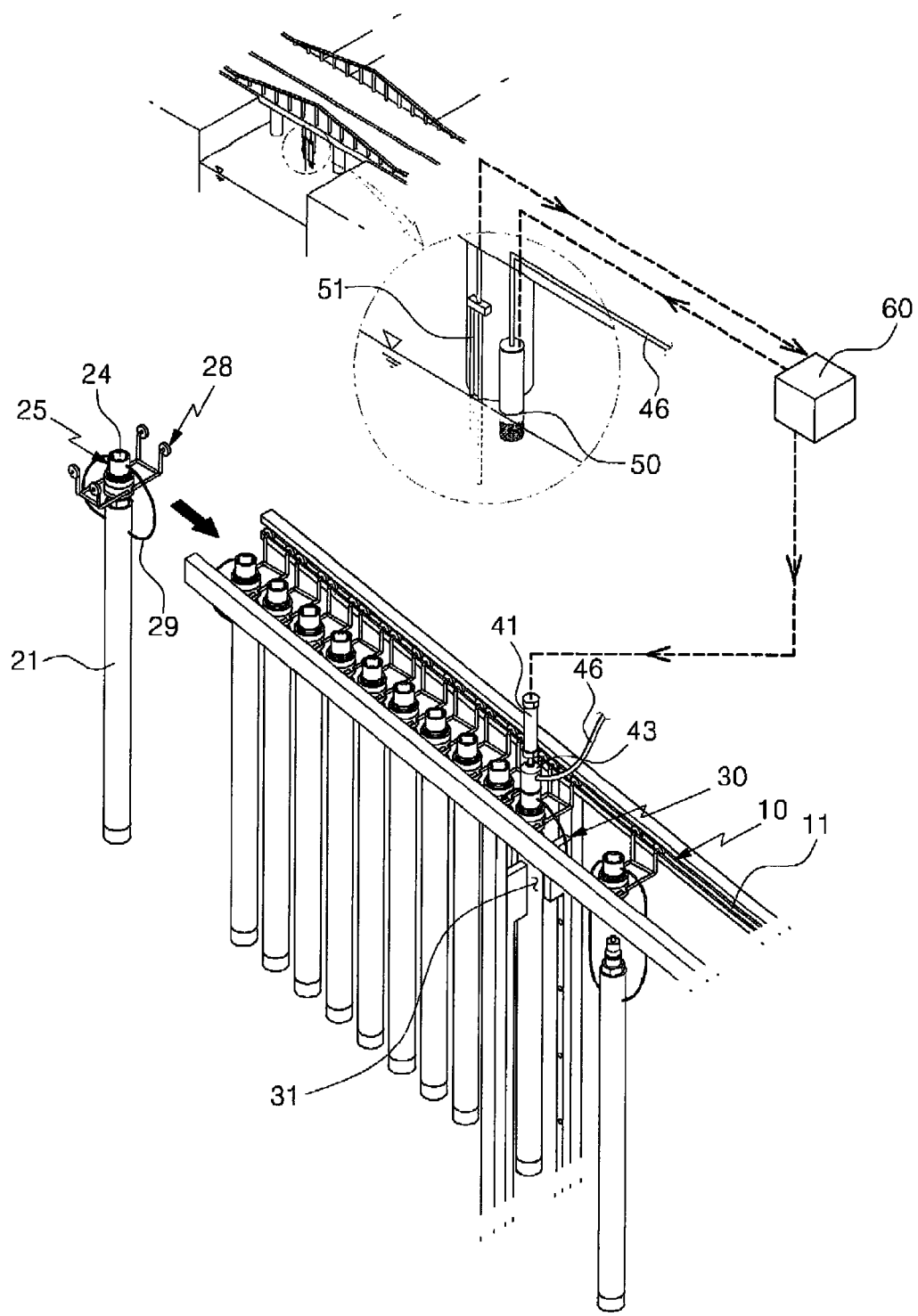
FIG. 1 is a perspective view illustrating a sequential sampler for runoff water according to an embodiment of the present invention.

10: rail member
21: storage cylinder
23: plug
25: coupler unit
28: driver
30: stopper
40: device of supplying runoff water and inducing drop of storage cylinder
41: electric actuator unit
43: inlet
45: control valve
50: intake pump
60: controller
20: storage member
22: shutter
24: socket
27: roller
29: wire
31: path way
42: power supply
44: bypass pipe
46: inlet hose
51: rainfall sensor

DETAILED DESCRIPTION OF THE INVENTION

Before describing the various embodiments according to the present invention, it will be understood that the application shall not be limited by the details of the configuration and arrangement of the elements set forth in the following detail description of drawings. The present invention may be realized in various other embodiments and may be performed in diverse methods. It will be understood that the terms such as directions of devices or elements (for example "front", "back", "up", "down", "top", "bottom", "left", "right", "lateral" and so on) and the like are used to simplify the explanation of the present invention and shall not be interpreted as having meaning that related devices or elements should have such particular directions. Further, the terms like "first" and "second" used in the specification and claims for explanation are not intended to represent or mean a relative importance or any other purpose.

The present invention has following characteristics to accomplish the object described above.

The present invention will now be described more fully hereinafter with reference to the accompanying drawings, in which preferred embodiments of the invention are shown. It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

Accordingly, since the embodiments set forth in the present specification and the configurations illustrated in the drawings are shown by way of example and do not represent all the technological spirit of the present invention, it should be understood that embodiments of the present invention are capable of various modifications, equivalents, and alternatives at the time of present application.

Figure 2:
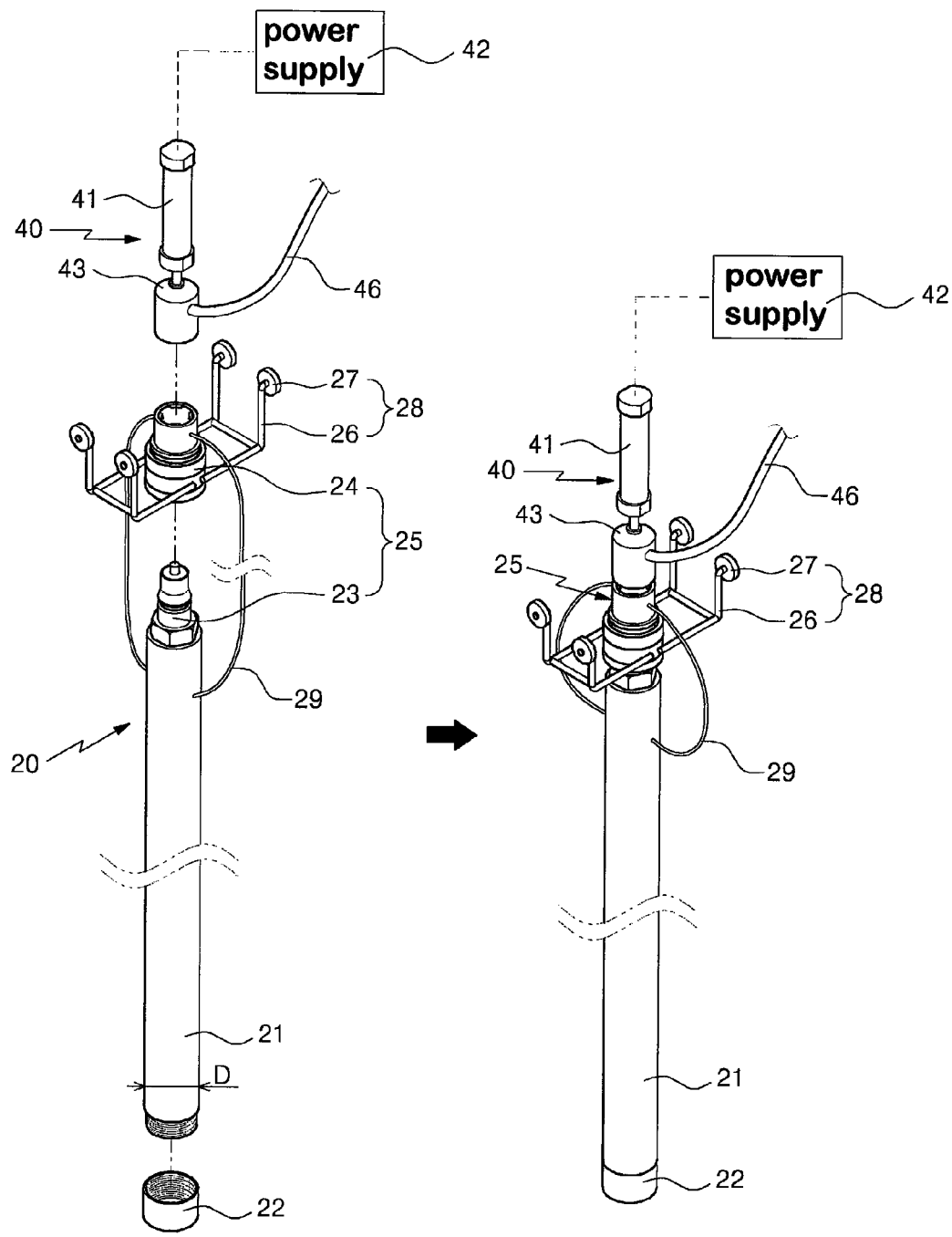
FIG. 2 is a perspective view illustrating a storage member and a device of supplying runoff water and inducing drop of storage cylinder according to an exemplary embodiment of the present invention.
Figure 3:
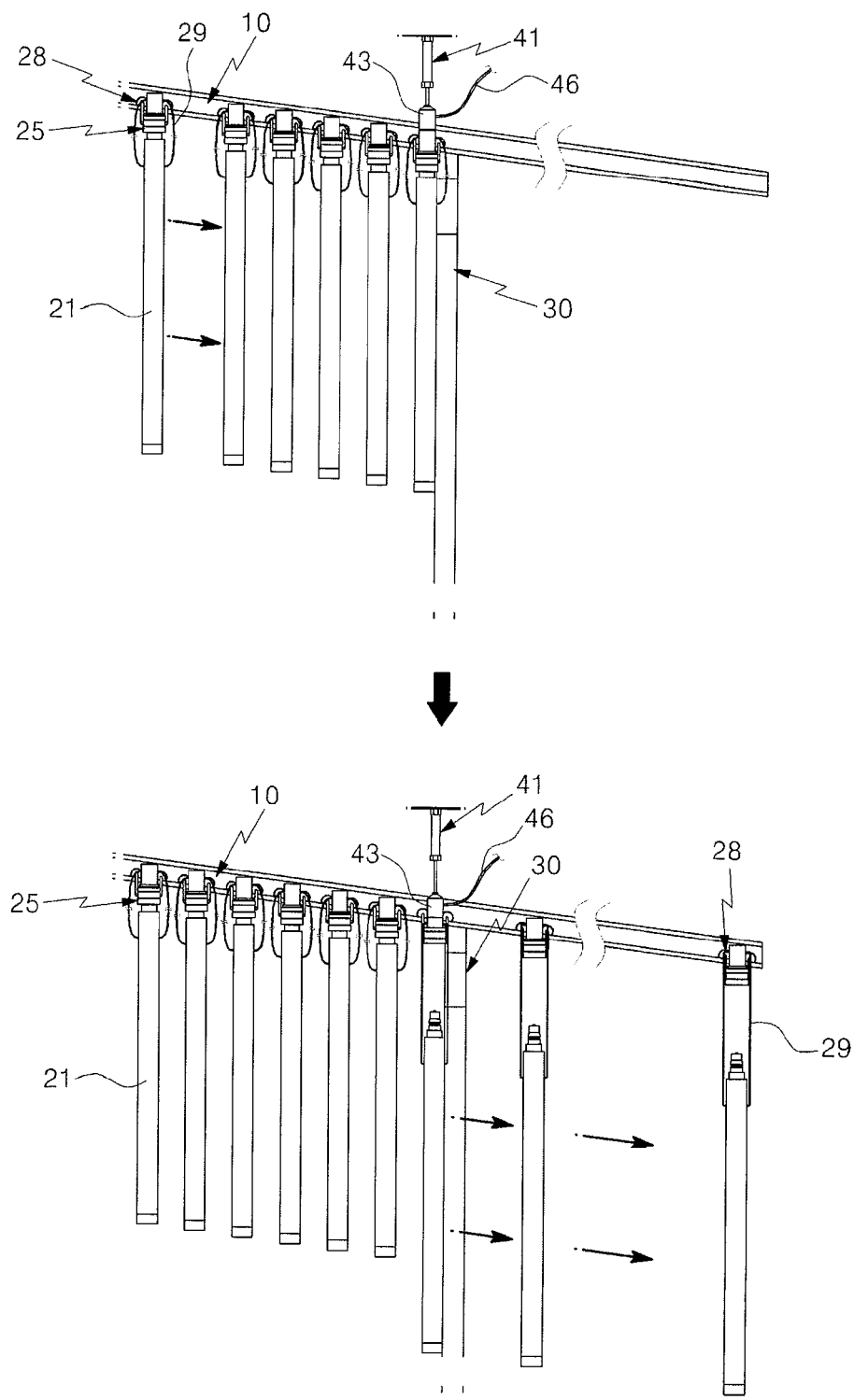
FIG. 3 is a side view illustrating a separation of a storage cylinder by device of supplying runoff water and inducing drop of storage cylinder according to an exemplary embodiment of the present invention.
Figure 4:
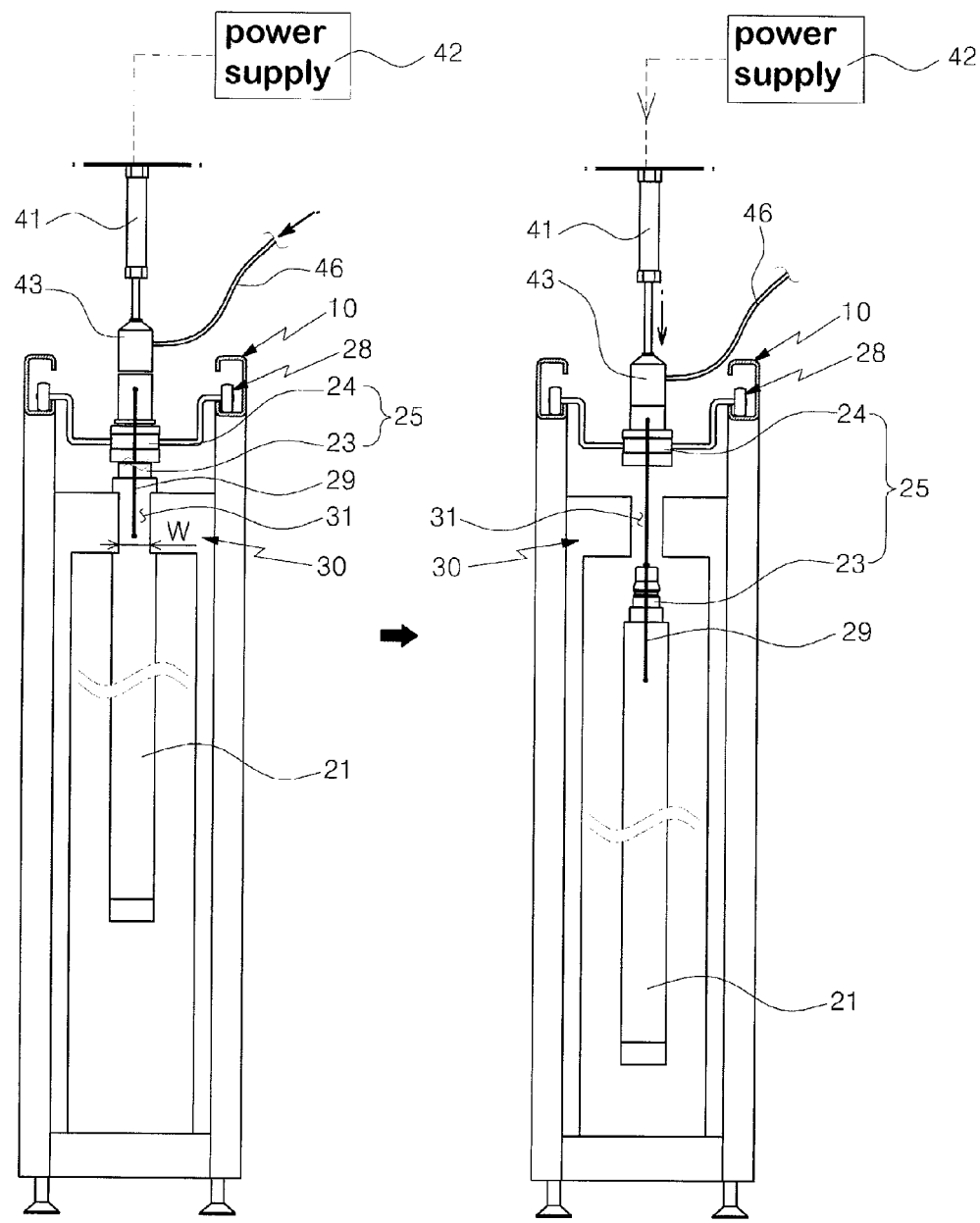
FIG. 4 is a front view of FIG. 3.
Figure 5:
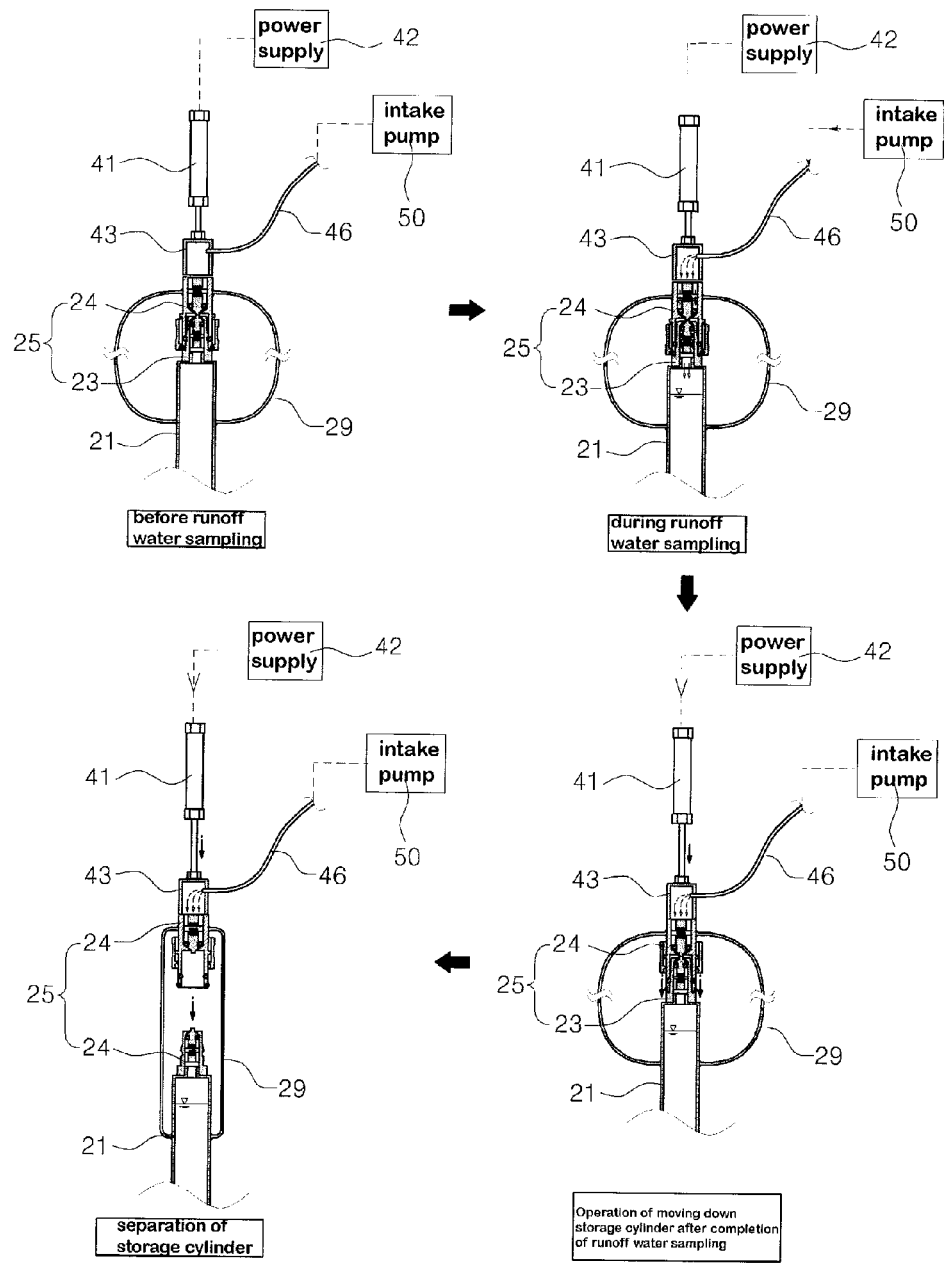
FIG. 5 is a view illustrating an operation of the sequential sampler for runoff water according to an exemplary embodiment of the present invention.

Hereinafter, a sequential sampler for runoff water according to a preferable embodiment of the present invention will be described in detail referring to FIGS. 1 through 5.

As illustrated, the sequential sampler for runoff water includes a rail member (10), a storage member (20), a stopper (30), a device of supplying runoff water and inducing drop of storage cylinder (40), an intake pump (50) and a controller (60).

The rail members (10) formed of plural rows of rails (11) face each other with a certain gap of separation. Such rail members (11) are sloped downward in one direction to move the storage member (20) to be described later downward along the rail member (10).

Height of either end of the rail member (10) can be controlled to adjust a downward angle of the rail member (10).

The said storage member (20) is to move downward along the said rail member (10) and formed of a storage cylinder (21), a coupler unit (25), a driver (28) and a wire (29).

The storage cylinder (21) that stores runoff water has circular round pipe shape open at its opposite ends. A shutter (22) of cover type capable to be open and closed is detachably coupled at a lower end portion of the storage cylinder (21) for discharge of runoff water stored inside or for convenient cleaning.

The coupler unit (25) is coupled at an upper end portion of the storage cylinder (21). The coupler unit (25) includes a plug (23) coupled integrally at an upper end portion of the storage cylinder (21) and a socket (24) detachably coupled with the plug (23). When the socket (24) and the plug (23) are coupled, the socket (24) and the plug (23) are communicated. Then, the socket (24) coupled at the upper end portion of the coupler unit (25) becomes to have an open shape and allows the runoff water to inflow and be stored inside the storage cylinder (21). When the socket (24) is separated from the plug (23) of the storage cylinder (21), one end portion of the socket (24) is sealed and operated to shut the runoff water inflow and leak off. A detail description of the coupler unit (25) is omitted since it is a known art.

The driver (28) is formed extended to both sides of the socket (24) to detachably couple with the plug (23) of the storage cylinder (21). In detail, the driver includes; a plurality of support bodies (26) formed extended to both sides from an outer circumference surface of the socket (24); and rollers (27) formed rotatable at end portions of the plurality of support bodies (26).

That is, the plurality of rollers (27) is installed to correspond with the plural rows of rails (11) respectively so that the storage member (20) can move in a length direction of the downward-sloped rail member (10).

Opposite ends of the wire (29) are fixed at an outer circumference surface of the said socket (24) and an outer circumference of the storage cylinder (21) storing the runoff water. When the storage cylinder (21) formed with the plug (23) is separated from the socket (24) and falls down, the wire (29) formed for the storage cylinder (21) to be dangled after falling down a certain distance enables the storage cylinder (21) to pass through the stopper (30).

The stopper (30) is installed upright at a middle portion of the said rail member (10) to intermit a movement of plural storage members (20) moving along the downward direction of the rail member (10).

In more detail, after intermitting a movement of the plural storage members (20) moving downward along the rail member (10) at a front portion of the stopper (30) to sequentially stand by the plural storage members (20) at the front portion of the stopper (30), the runoff water starts to inflow into from the first intermitted storage member (20), then, the plug (23) of the storage cylinder (21) is separated from the socket (24) and moves to a rear portion of the stopper (30).

For this, a path way (31) is formed open in vertical direction at a middle portion of the stopper (30). The path way (31) has a width (W) smaller than a diameter (D) of the storage cylinder (21) so that the storage member (20) cannot escape the path way (31) but stops in front of the open path (31) of the stopper (30).

Then, into an open upper portion of the storage cylinder (21) where the socket (24) and the plug (23) are connected, the runoff water inflows by the device of supplying runoff water and inducing drop of storage cylinder (40) (to be described later). After elapsing a predetermined time, the socket (24) and the plug (23) are separated. Then, the storage cylinder (21) falls down and is dangled to the socket (24) by the wire (29).

The storage cylinder (21) that could not pass the path way (31) is now in a dangled state by being disposed lower that the stopper (30) that blocked the storage cylinder (21). Then, the wire (29) that connects the storage cylinder (21) and the socket (24) is disposed at the front portion of the path way (31) to pass the path way (31), and eventually the storage member (20) passes the stopper (30).

The passed storage member (20) moves along the downward-sloped rail member (10) is caught and stopped at a lowest end of the rail member (10). Then, after repeating the above operation and passing the stopper (30), the other storage members (20) also stop at the one end of the rail member (10).

The device of supplying runoff water and inducing drop of storage cylinder (40) is installed at a front upper end portion of the stopper (30) and inflows the runoff water into the said storage member (20). The device of supplying runoff water and inducing drop of storage cylinder (40) includes an electric actuator unit (41) and an inlet (43) to perform a role of separating the plug integrally coupled with the storage member (20) from the socket (24).

The electric actuator unit (41) is installed in a housing installed with the rail member (10) of the present invention, a ceiling and the like, downward vertically. The electric actuator (41) moves up and down. (A separately installed battery or solar energy is used for a power supply (42).)

The inlet (43) is open to its lower surface with a hollow pipe shape and fixedly installed at a lowest end portion of the electric actuator unit (41). Since the inlet (43) is formed integrally with the electric actuator unit (41), the inlet (41) moves up and down to be operated in accompanied motion identical with the electric actuator unit (41) when the electric actuator (41) moves up and down.

The described inlet (43) is disposed close to the upper end portion of the first storage member (20) that is intermitted its movement by the stopper (30) and stands by. Particularly, the inlet (43) is disposed above the socket (24) of the storage member (20).

The described inlet (43) performs a role of inflowing the runoff water to the storage cylinder (21) of the storage member (20) in a state that the socket (24) and the plug (23) are coupled. One end of a flexible inlet hose (46) connected to an intake pump (50), to be described later, is installed at an outer circumference surface of the inlet (43). The runoff water that inflows from the intake pump (50) passes the communicated socket (24) and the plug (23) and is stored inside the storage cylinder (21) after inflowing to the inlet (43).

Further, after elapsing a predetermined time to inflow the runoff water into the storage cylinder (21) preset by a user, the electric actuator (41) starts an operation of pressing and pushing the upper portion of the socket (24) by moving down the inlet (43), thereby the socket (24) coupled with the plug (23) is separated from the plug (23) and the storage cylinder (21) which upper end portion is coupled with the plug (23) falls downward.

In other words, the inlet (43) performs roles of inflowing the runoff water inside the storage cylinder (21) as well as separating of the socket (24) and the plug (23).

The intake pump (50) performs a role of supplying the runoff water to the said device of supplying runoff water and inducing drop of storage cylinder (40) during a rainfall.

The controller (60) is electrically connected with the electric actuator unit (41), and a rainfall sensor (51) to control an up and down operation of the electric actuator unit (41), thereby enabling sequential sampling for runoff water in the plural storage members (20) in a predetermined time preset by a user.

As described above, the present invention can sequentially sample runoff water by perceiving rainfall through automatically operating the sequential sampler for runoff water when rain falls.

Further, the present invention can automatically and conveniently collect samples of runoff water by dividing runoff water with respect to time, thereby increasing accuracy of the collected runoff water quality analysis.

Further, a manual job by an operator is not required for sequential sampling of runoff water, thereby reducing human and material resources.

Further, the present invention seals the storage cylinder after sampling runoff water, thereby reducing loss from evaporation of runoff water and volatile organic material.

While the present invention has been particularly shown and described with reference to limited exemplary embodiments and drawings, it will be understood by those of ordinary skill in the art that various changes in form and details may be made therein without departing from the spirit and scope of the present invention as defined by the following claims.

What is claimed is:

1. A sequential sampler for runoff water, comprising:
 a rail member (10) installed to be sloped downward toward one direction;
 a storage member (20) that moves in a downward direction of the rail member (10) and is configured of a storage cylinder (21) that forms a coupler unit (25) at an upper end portion of the storage member (20);
 a stopper (30) installed at a middle portion of the rail member (10) to intermit a transfer of the storage member (20);
 a device of supplying runoff water and inducing drop of storage cylinder (40) disposed at a front portion of the stopper (30) to inflow runoff water to the storage member (20) and to separate the storage cylinder (21) of the storage member (20) stored with runoff water; and
 an intake pump (50) to collect and provide runoff water for the device of supplying runoff water and inducing drop of storage cylinder (40).

2. The sampler according to claim 1,
 wherein the storage member (20) comprises:
 the storage cylinder (21) provided with a shutter (22) at a lower end portion of the storage member (20);
 the coupler unit (25) comprising a plug (23) coupled integrally at an upper end portion of the storage cylinder (21), and a socket (24) correspondingly and detachably coupled with the plug (23);
 a driver (28) formed rotatable and extended to both sides of the socket (24) to correspond with the rail member (10); and
 a wire (29) connecting the socket (24) and the storage cylinder (21).

3. The sampler according to claim 1,
 wherein the device for supplying runoff water and inducing drop of storage cylinder (40) comprises:
 an electric actuator unit (41) that moves up and down; and
 an inlet (43) that operates in an up and down movement together with the electric actuator unit (41) at a lower end portion of the electric actuator unit (41), and moves down to press and separate the socket (24) of the connecting member from the plug (23).

4. The sampler according to claim 1,
wherein the stopper (30) comprises:
a pathway (31) open in vertical direction at a middle portion of the stopper (30), and the pathway (31) has a width (W) smaller than a diameter (D) of the storage cylinder (21) so that the storage member (20) passes, only when the storage cylinder (21) is separated and dangled at the socket (24) of the coupler unit (25) by the wire (29).

5. The sampler according to claim 3 further comprising;
a controller (60) that sequentially samples and collects runoff water at the plurality of storage members (20) in a predetermined time interval set by a user through controlling moving up and down operation of the electric actuator unit (41), according to whether there is rainfall or not.

* * * * *